United States Patent
Shinoda

(10) Patent No.: US 10,132,744 B2
(45) Date of Patent: Nov. 20, 2018

(54) METHOD FOR MANAGING LUBRICANT OIL, AND METHOD FOR PREDICTING LIFE OF LUBRICANT OIL

(71) Applicant: IDEMITSU KOSAN CO., LTD., Chiyoda-ku (JP)

(72) Inventor: Jitsuo Shinoda, Ichihara (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 0 days.

(21) Appl. No.: 15/542,755

(22) PCT Filed: Jan. 13, 2016

(86) PCT No.: PCT/JP2016/050833
§ 371 (c)(1),
(2) Date: Jul. 11, 2017

(87) PCT Pub. No.: WO2016/114302
PCT Pub. Date: Jul. 21, 2016

(65) Prior Publication Data
US 2018/0003618 A1    Jan. 4, 2018

(30) Foreign Application Priority Data

Jan. 14, 2015 (JP) ................. 2015-005419

(51) Int. Cl.
*G01T 1/169* (2006.01)
*G01N 21/25* (2006.01)
(Continued)

(52) U.S. Cl.
CPC ........... *G01N 21/251* (2013.01); *B01D 61/00* (2013.01); *G01J 3/50* (2013.01); *G01N 21/25* (2013.01);
(Continued)

(58) Field of Classification Search
CPC ............... G01N 21/3577; G01N 33/28; G01N 2021/3595; G01N 21/35; G01N 21/94;
(Continued)

(56) References Cited

U.S. PATENT DOCUMENTS 8,390,796 B2 * 3/2013 Honda .................. G01N 21/27
356/71
8,464,576 B2 * 6/2013 Okuyama ................ F01M 1/18
73/53.01
(Continued)

FOREIGN PATENT DOCUMENTS

JP      63-63967 A     3/1988
JP      11-194124 A    7/1999
(Continued)

OTHER PUBLICATIONS

Title: Standard Test Method for Measurement of Lubricant Generated Insoluble Color Bodies in In-Service Turbine Oils using Membrane Patch Colorimetry (ASTM D7843), date: 2012, Publisher: ASTM committee.*
(Continued)

*Primary Examiner* — Taeho Jo
(74) *Attorney, Agent, or Firm* — Oblon, McClelland, Maier & Neustadt, L.L.P.

(57) ABSTRACT

A management method of a lubricating oil of the invention is a method of managing a lubricating oil by determining a degradation degree of the lubricating oil containing an antioxidant, specifically, according to determination methods a and b below. The determination method a includes: measuring an infrared ray absorption spectrum of the lubricating oil using a Fourier transform infrared spectrometer; and calculating a total content of the antioxidant and an altered substance having an antioxidant function to determine a deterioration degree of the lubricating oil from the obtained content. The determination method b includes:

(Continued)

filtrating the lubricating oil with a filter; subsequently measuring a color difference of substances captured by the filter using a colorimeter, or measuring a color difference of the lubricating oil using the colorimeter; and determining a degradation degree of the lubricating oil and a mixture degree of foreign substances based on the obtained color difference.

5 Claims, 7 Drawing Sheets

(51) Int. Cl.
    *G01J 3/50*     (2006.01)
    *B01D 61/00*     (2006.01)
    *G01N 21/3577*     (2014.01)
    *G01N 21/94*     (2006.01)
    *G01N 33/28*     (2006.01)
    *G01N 21/35*     (2014.01)

(52) U.S. Cl.
    CPC ......... *G01N 21/3577* (2013.01); *G01N 21/94* (2013.01); *G01N 33/2835* (2013.01); *G01N 33/2888* (2013.01); *G01N 2021/3595* (2013.01); *G01N 2201/12* (2013.01)

(58) Field of Classification Search
    CPC . G01N 33/2858; G01N 33/2888; B01D 61/00
    USPC ........................................................ 250/301
    See application file for complete search history.

(56) References Cited

U.S. PATENT DOCUMENTS

| | | | | |
|---|---|---|---|---|
| 8,829,904 | B2* | 9/2014 | White | G01N 24/08 324/318 |
| 9,804,142 | B2* | 10/2017 | Basu | G01N 33/2888 |
| 2003/0222656 | A1* | 12/2003 | Phillips | G01N 27/02 324/605 |
| 2004/0204326 | A1* | 10/2004 | Costello | C10M 141/02 508/545 |
| 2010/0116022 | A1* | 5/2010 | Cummings | G01N 33/2876 73/23.41 |
| 2010/0180671 | A1* | 7/2010 | Okuyama | F01M 1/18 73/53.05 |
| 2011/0155925 | A1* | 6/2011 | Ukon | G01N 21/6408 250/458.1 |
| 2012/0086942 | A1* | 4/2012 | Honda | G01N 21/27 356/436 |
| 2014/0099728 | A1* | 4/2014 | Selby | G01N 33/2805 436/147 |
| 2016/0003794 | A1* | 1/2016 | Basu | G01N 33/2888 702/30 |

FOREIGN PATENT DOCUMENTS

| | | |
|---|---|---|
| JP | 2001-74728 A | 3/2001 |
| JP | 2004-212292 A | 7/2004 |
| JP | 5190660 B2 | 4/2013 |

OTHER PUBLICATIONS

International Search Report dated Mar. 22, 2016, in PCT/JP2016/050833, filed Jan. 13, 2016.

Shinoda et al., "New Management Method of Turbine Oil", Idemitsu Tribo Review, No. 37-2014, 2014. with partial English translation. 7 pages.

"Agilent 5500 Series FTIR Operation Manual", Agilent Technologies, Fifth Edition, Sep. 2013, 54 pages.

* cited by examiner

METHOD FOR MANAGING LUBRICANT OIL, AND METHOD FOR PREDICTING LIFE OF LUBRICANT OIL

TECHNICAL FIELD

The present invention relates to a method for managing a lubricating oil and a method for predicting a lifetime of the lubricating oil.

BACKGROUND ART

It is crucial to determine a degradation degree of a lubricating oil in order to prevent an in-use machine from being broken and to judge a timing of changing the lubricating oil. For this judgment, the degradation degree of the lubricating oil is determined according to various methods. Examples of the methods include a method of measuring a kinematic viscosity change ratio, acid value increasing amount, foaming amount, water amount, anticorrosive performance, ASTM color, Rotary Pressure Vessel Oxidation Test (RPVOT) residual ratio, and the like described in ASTM D4378. In addition to the above method, the examples of the methods of determining the degradation degree further include, as an easy evaluation method: a method of measuring an antioxidant residual ratio by a voltammetry method described in ASTM D6810 and D6971; and a method of measuring a color difference (ΔE) by a color difference method described in ASTM D7843.

Further, in a turbine oil and wind-power generation, it is crucial to manage conditions of the lubricating oil in order to stably generate power. This is because an abrupt halt of power generation equipment caused by an oil solution or mixed-in foreign substances other than the oil solution significantly affects an economic activity and a civic lifetime. Moreover, in addition to managing conditions of the lubricating oil, a method of predicting a lifetime expectancy of the lubricating oil is also required.

However, in the method described in ASTM D4378, various measurements are required, a condition of the lubricating oil changes between at a sampling and at a measurement, and the measurements require skillfulness. Moreover, since the residual amount of the antioxidant contained in the lubricating oil is not determined in the method described in ASTM D4378, a substantial oxidation stability of the lubricating oil is unclear. Accordingly, the amount of the antioxidant needs to be separately determined and is generally measured by high speed liquid chromatography (HPLC). As a method using HPLC, for instance, there has been proposed a method including determining the amount of the antioxidant using HPLC and determining the amount of the antioxidant by gel permeation chromatography-ultraviolet photometric detector method (see Patent Literature 1).

Moreover, it has been proposed to subject the used lubricating oil to multivariable analysis using a near-infrared spectrum to predict properties and performance (see Patent Literature 2).

CITATION LIST

Patent Literature(s)

Patent Literature 1: JP2001-074728A
Patent Literature 2: JP11-194124A

SUMMARY OF THE INVENTION

Problem(s) to be Solved by the Invention

However, in HPLC, although the amount of the antioxidant can be determined when the antioxidant has an original structure, when the antioxidant is altered to a substance although still having an antioxidant function, it is extremely difficult to determine an amount of the altered substance. Moreover, the method disclosed in Patent Literature 1 requires a huge work load for evaluation.

Further, in the method of measuring the antioxidant residual ratio by the voltammetry method described in ASTM D6810 and D6971, a correlation with an RPVOT value for measuring an oxidation lifetime (ASTM D2272) is insufficient, so that the degradation degree is insufficiently determined.

In the near-infrared spectrum, even though the RPVOT value can be predicted, a lifetime of the lubricating oil in consideration of the antioxidant ability cannot be predicted. Moreover, since a spectrum derived from the antioxidant is close to a spectrum of another component, the amount of the antioxidant cannot be accurately determined.

An object of the invention is to provide a management method of a lubricating oil, the method capable of easily determining a degradation degree of the lubricating oil with a high accuracy, and a lifetime expectancy prediction method of the lubricating oil.

Means for Solving the Problem(s)

According to an aspect of the invention, a management method of a lubricating oil includes: determining a degradation degree of the lubricating oil containing an antioxidant according to a determination method a and a determination method b, the determination method a including: measuring an infrared ray absorption spectrum of the lubricating oil using a Fourier transform infrared spectrometer; and calculating a total content of the antioxidant and an altered substance having the same functional group as the antioxidant to determine a deterioration degree of the lubricating oil from the total content, the determination method b including: filtrating the lubricating oil with a filter; subsequently measuring a color difference of substances captured by the filter using a colorimeter, or measuring a color difference of the lubricating oil using the colorimeter; and determining a degradation degree of the lubricating oil and a mixture degree of foreign substances based on the color difference of the substances or the color difference of the lubricating oil.

According to another aspect of the invention, in a lifetime expectancy prediction method of a measurement oil by determining a degradation degree of the measurement oil in a form of a used lubricating oil including an antioxidant, the method includes: a first step of obtaining a determination value of the measurement oil according to a determination method a and a determination method b below, a second step of subjecting the measurement oil to a degradation process for a predetermined time until the lubricating oil reaches a threshold value representing a usage limit of the lubricating oil, and obtaining a determination value of the measurement oil after being subjected to the degradation process according to the determination method a and the determination method below, and a third step of predicting a lifetime expectancy of the measurement oil based on a time of the degradation process in the second step, the determination value, which is obtained in the second step, of the measurement oil after being subjected to the degradation process, and the determination value, which is obtained in the first step, of the measurement oil, the determination method a including: measuring an infrared ray absorption spectrum of the lubricating oil using a Fourier transform infrared spectrometer; and calculating a total content of the antioxidant and an altered substance having the same functional group as the antioxidant to determine a deterioration degree of the lubricating oil from the total content, the determination method b including: filtrating the lubricating oil with a filter; subsequently measuring a color difference of substances captured by the filter using a colorimeter, or measuring a color difference of the lubricating oil using the colorimeter; and determining a degradation degree of the lubricating oil and a mixture degree of foreign substances based on the color difference of the substances or the color difference of the lubricating oil.

According to the above aspects of the invention, a management method of a lubricating oil, the method capable of easily determining a degradation degree of the lubricating oil with a high accuracy, and a lifetime expectancy prediction method of the lubricating oil can be provided.

BRIEF DESCRIPTION OF DRAWING(S)

DESCRIPTION OF EMBODIMENT(S)

Figure 1:
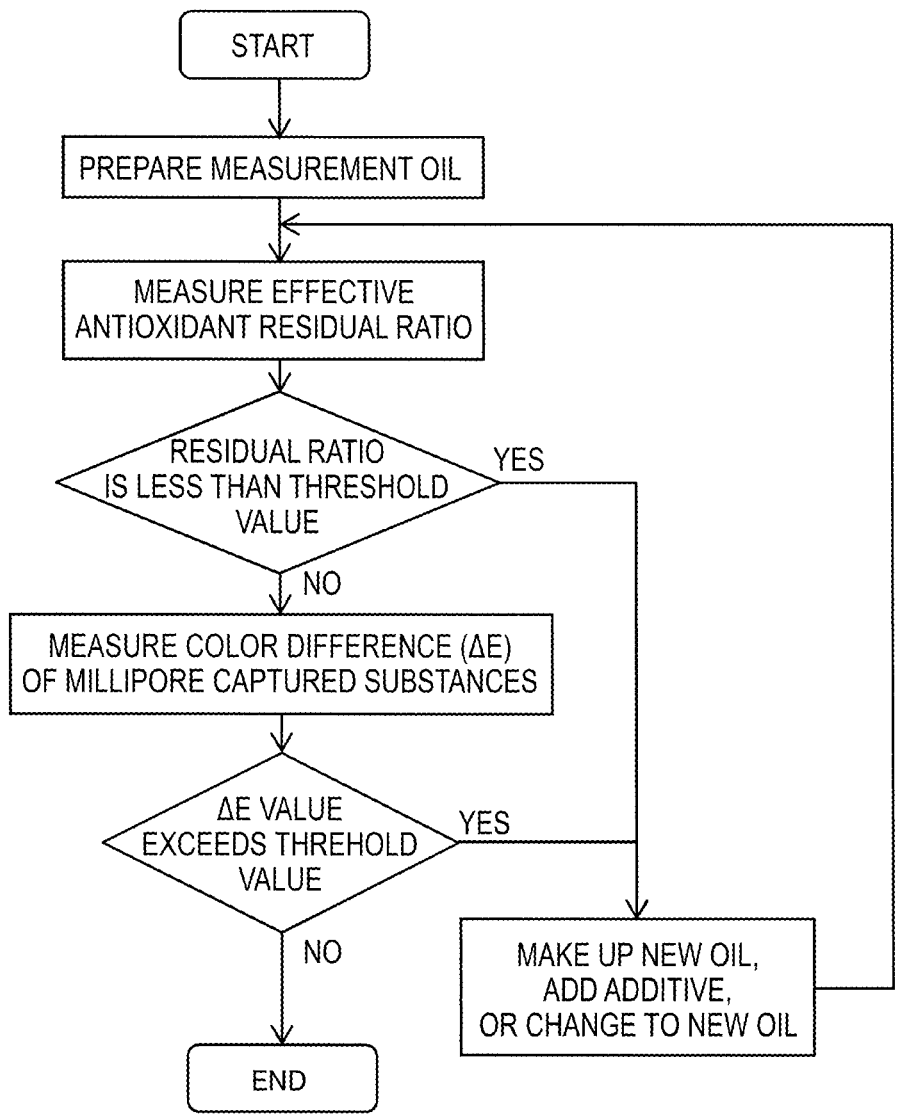
FIG. 1 is a flowchart showing a method for managing a lubricating oil in an exemplary embodiment of the invention.

Exemplary embodiment(s) of the invention will be described in detail below. The exemplary embodiment(s) described below shows a suitable example of the invention and includes various preferable limitations. However, the scope of the invention is by no means limited to the exemplary embodiment(s) unless specifically described for limiting the invention in the description below.

Management Method of Lubricating Oil

Firstly, a management method of a lubricating oil in an exemplary embodiment will be described.

The management method of the lubricating oil in the exemplary embodiment is a method of managing a lubricating oil by determining a degradation degree of the lubricating oil containing an antioxidant, specifically, according to both of a determination method a and a determination method b described below.

The lubricating oil used in the exemplary embodiment contains an antioxidant. Examples of the antioxidant include: a radical scavenger such as an amine antioxidant, phenolic antioxidant, and sulfur antioxidant; and a peroxide decomposer such as ZnDTP (zinc alkyl dithiophosphate) and a phosphorus antioxidant. One of the antioxidants may be used alone or two or more thereof may be used in combination.

Determination Method a

The determination method a includes: measuring an infrared ray absorption spectrum of the lubricating oil using a Fourier transform infrared spectrometer; and calculating a total content of the antioxidant and an altered substance having an antioxidant function to determine a degradation degree of the lubricating oil from the obtained content. The altered substance having the antioxidant function has the same functional group as that of the in-use antioxidant and refers to a compound in a form of a dimer, trimer or other structures, the compound being formed due to thermal degradation and oxidation degradation of the lubricating oil in use.

Since the total content of the antioxidant and the altered substance having the antioxidant function can be determined by the determination method a, a degradation degree of the lubricating oil can be determined in terms of the antioxidant function. Specifically, when the obtained content is less than a predetermined threshold value (i.e., a reference value for usage management and a reference value for oil change), the lubricating oil can be determined to reach a usage limit.

Herein, the threshold value indicates that a machine is likely to be damaged when the lubricating oil having a lowered performance is kept being used. In the threshold value, the reference value for usage management (hereinafter, also referred to as the usage management reference value) is a value to be daily managed and a value indicating that a trouble may occur in use when the content falls below the usage management reference value. The reference value for oil change (hereinafter, also referred to as the oil change reference value) is a value indicating that the oil reaches the usage limit when the lubricating oil performance is extremely lowered and the content falls below the oil change reference value.

Items for managing the reference values include an RPVOT value, acid value, sludge amount, water amount, and the like. Particularly, the RPVOT value is crucial for management. A setting of the reference values are determined depending on a usage condition and may be independently determined.

The Fourier transform infrared spectrometer (FTIR) is preferably one satisfying the following specification and is exemplified by a small-sized FTIR device "DialPath" manufactured by Agilent Technologies. Interference pattern: high-throughput Michelson interferometer Resolution: 4 $cm^{-1}$ or more Cell material: ZnSe With this FTIR device, a light path length can be made constant by DialPath cells mounted in the FTIR device and can be measured without receiving any influence from moisture and carbon dioxide contained in air. Moreover, the FTIR device is tightly sealed, thereby allowing a measurement without receiving any influence from air. A Zinc Selenide (ZnSe) substrate is used as a substrate of a beamsplitter of the interferometer and has characteristics that the substrate does not deliquesce in moisture in air.

By analyzing an infrared ray absorption spectrum measured using the FTIR device, the total content of the antioxidant and the altered substance having the antioxidant function can be calculated. Specifically, the total content of the antioxidant and the altered substance having the antioxidant function can be calculated based on a change in a height and an area of a peak of a functional group derived from the antioxidant function of the antioxidant. For instance, in a case of an amine antioxidant, the content can be calculated based on a change in a peak (wave number: from 1550 cm$^{-1}$ to 1640 cm$^{-1}$, from 3300 cm$^{-1}$ to 3500 cm$^{-1}$) of an amino group. In a case of a phenolic antioxidant, the content can be calculated based on a change in a peak (wave number: from 3600 cm$^{-1}$ to 3650 cm$^{-1}$) of phenol.

Determination Method b

The determination method b is a (i) method or a (ii) method described below.

The (i) method includes: filtrating the lubricating oil with a filter; subsequently measuring a color difference of substances captured by filtration using a colorimeter; and determining a degradation degree of the lubricating oil and a mixture degree of foreign substances based on the obtained color differences.

The (ii) method includes: measuring a color difference ($\Delta E$ and/or a maximum color difference) of the lubricating oil (lubricating oil liquid) using a colorimeter; and determining a degradation degree of the lubricating oil and a mixture degree of foreign substances based on the obtained color differences.

Herein, the substances captured by filtration refer to degraded altered substances derived from the lubricating oil, sludge of the degraded altered substances, internal fouling substances (e.g., metal pieces generated after a device component is worn or peeled off), and substances (e.g., dust and dirt such as sands) entering from the outside, as a result of using the lubricating oil containing an additive (e.g., antioxidant). In the above (ii) method, the lubricating oil (lubricating oil liquid) itself is used as a sample oil and a color difference ($\Delta E$ and/or a maximum color difference) of the lubricating oil is measured using the colorimeter. According to the determination method b, a degradation degree of the lubricating oil and a mixture degree of foreign substances can be determined in terms of the alteration of the lubricating oil. Specifically, when the obtained color difference exceeds a predetermined threshold value (the usage management reference value, the oil change reference value), the lubricating oil can be determined to reach a usage limit.

Herein, the threshold value indicates that a machine is likely to be damaged when the lubricating oil whose performance is lowered is kept being used. With respect to the threshold, the usage management reference value is a value to be daily managed and a value indicating that a trouble may occur in use when the color difference exceeds the usage management reference value. The oil change reference value is a value indicating that the oil reaches the usage limit when the lubricating oil performance is extremely lowered and the color difference exceeds the oil change reference value.

Items for managing the reference values include an RPVOT value, acid value, sludge amount, water amount, and the like. Particularly, the RPVOT value and the sludge amount are crucial for management. A setting of the reference values are determined depending on a usage condition and may be independently determined.

A mean hole diameter of the filter for capturing the sludge is preferably in a range from 0.2 μm to 3.0 μm, more preferably in a range from 0.3 μm to 2.0 μm, further preferably in a range from 0.45 μm to 1.0 μm. The filter is exemplified by a membrane filter manufactured by Millipore Corporation and one manufactured by ADVANTEC Toyo Kaisha, Ltd.

The method of measuring the color difference of the substances captured by filtration of the lubricating oil is exemplified by a method disclosed in JP Patent No. 5190660 (CPA method) and a method in accordance with Membrane Patch Colorimetry (MPC) method of a turbine oil described in ASTM D7843. Specifically, a color difference ($\Delta E$) of the substances captured by filtration of the lubricating oil using the filter is measured using a colorimeter.

A filtration method is exemplified by a method conducted using a filter under measurement conditions described in JIS B9931. The colorimeter is exemplified by one for measuring a color difference in an RGB color space or an L*a*b* color space. Among the colorimeter, the colorimeter for measuring a color difference in the RGB color space is more preferable in order to determine a color difference represented by an absolute coordinate of three primary colors.

The colorimeter in the RGB color space is exemplified by a Colorimetric Patch Analyzer (CPA method) manufactured by Hitachi Metals, Ltd. and a lubricating oil condition monitoring sensor manufactured by Nabtesco Corporation. The colorimeter in the L*a*b* color space is exemplified by a spectrophotometer (MPC method) manufactured by Konica Minolta, Inc.

Management Method of Lubricating Oil

In the management method of the lubricating oil in the exemplary embodiment, the lubricating oil is managed by both of the determination method a and the determination method b. Specifically, the lubricating oil is managed by a process described in the flowchart of FIG. 1. However, a measurement order of the effective antioxidant residual ratio and the color difference of the substances captured by the Millipore filter may be reversed to manage the lubricating oil.

Specifically, when a determination value obtained by the determination method a is less than a predetermined threshold value (usage management reference value, oil change reference value), or when a determination value obtained by the determination method b exceeds a predetermined threshold value (usage management reference value, oil change reference value), the lubricating oil is determined to be degraded. When the lubricating oil is determined to reach the usage management reference value, a new oil (unused lubricating oil) is made up to the in-use oil (the used lubricating oil) or an additive concentrate containing an antioxidant at a high concentration is added to the in-use oil, thereby allowing a continuous use of the oil. When exceeding the oil change reference value, the in-use oil (the used lubricating oil) is replaced by a new oil (unused lubricating oil), thereby managing a lifetime of the lubricating oil.

In the management method of the lubricating oil in the exemplary embodiment, the degradation degree of the lubricating oil can be easily determined since both of the determination method a and the determination method b are simple methods.

In the management method of the lubricating oil in the exemplary embodiment, the degradation degree of the lubricating oil can be determined with a high accuracy since the degradation degree of the lubricating oil are determined in view of two different points using the two methods of the determination method a and the determination method b.

The management method of the lubricating oil in the exemplary embodiment can easily determine the degradation degree with a high accuracy, particularly, of a turbine oil, a gear oil for a windmill, and hydraulic fluid among the lubricating oil.

Lifetime Expectancy Prediction Method of Lubricating Oil

Next, a lifetime expectancy prediction method of the lubricating oil in the exemplary embodiment will be described.

Figure 2:
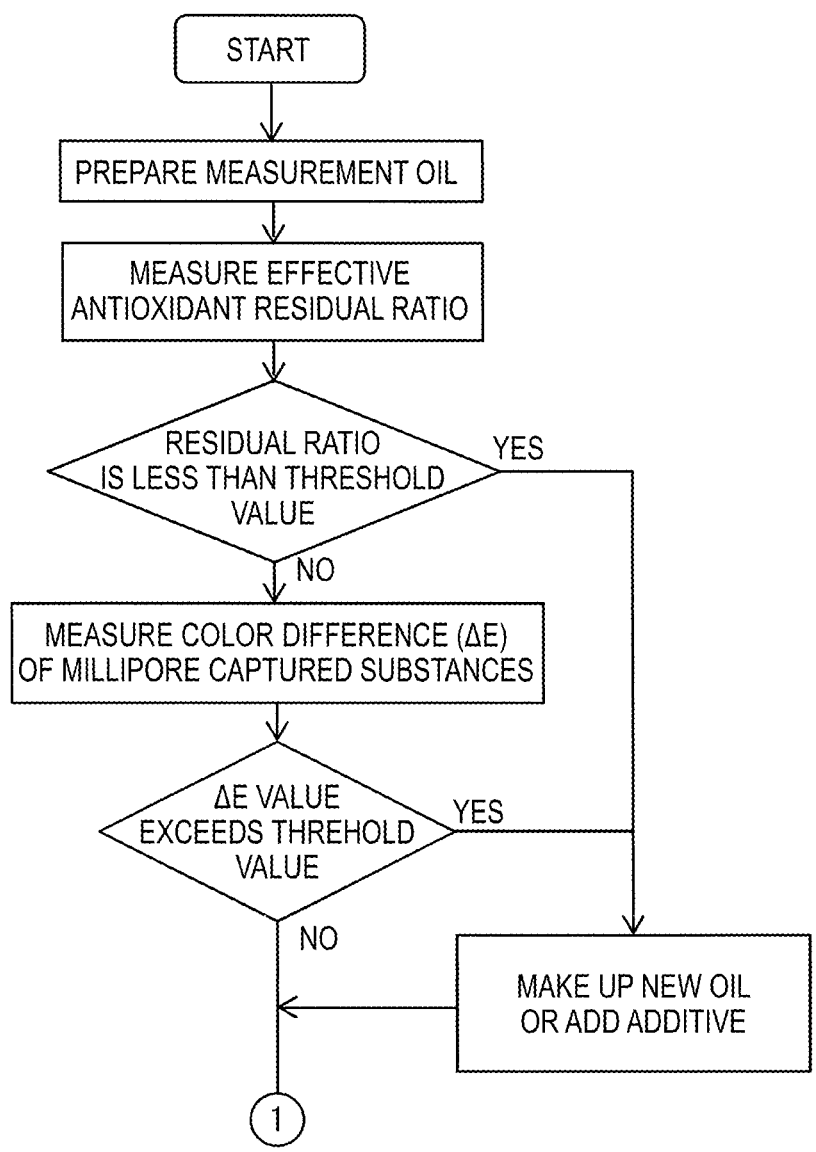
FIG. 2 is a flowchart showing a method for predicting a lifetime of the lubricating oil in the exemplary embodiment.
Figure 3:
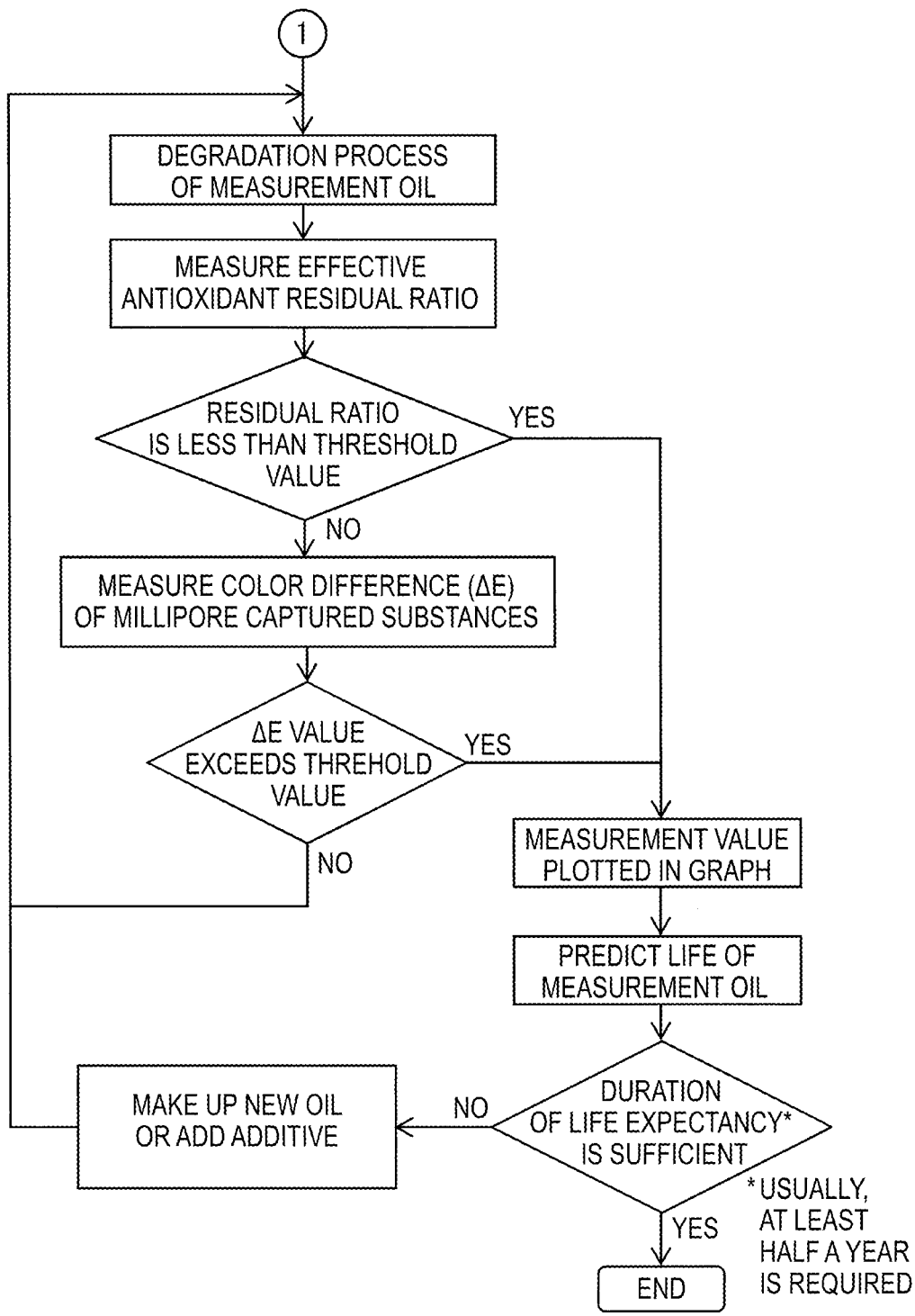
FIG. 3 is the flowchart (continued) showing the method for predicting the lifetime of the lubricating oil in the exemplary embodiment.

The lifetime expectancy prediction method of the lubricating oil in the exemplary embodiment predicts a lifetime expectancy of the lubricating oil by determining the degradation degree of the lubricating oil containing the antioxidant. The lifetime expectancy prediction method includes a first step, a second step and a third step described below. Specifically, the lifetime expectancy of the lubricating oil is predicted by a process described in the flowcharts of FIGS. 2 and 3. However, a measurement order of the effective antioxidant residual ratio and the color difference of the substances captured by the Millipore filter may be reversed to predict the lifetime expectancy of the lubricating oil.

The lubricating oil used in the exemplary embodiment contains an antioxidant. The same antioxidant as the antioxidant used in the management method of the lubricating oil in the exemplary embodiment is usable.

In the first step: a measurement oil for predicting the lifetime expectancy of the lubricating oil is prepared; and a determination value of the measurement oil is obtained by both of the determination method a and the determination method b.

The measurement oil for predicting the lifetime expectancy of the lubricating oil refers to: a lubricating oil actually used in a machine; a lubricating oil that is provided by making up a new oil to the used lubricating oil; and a lubricating oil that is provided by adding an additive concentrate containing an antioxidant at a high concentration to the used lubricating oil.

As the determination method a and the determination method b the same methods as the determination method a and the determination method b in the management method of the lubricating oil in the exemplary embodiment are applicable.

In the second step: the measurement oil for predicting the lifetime expectancy of the lubricating oil is subjected to a degradation process for a predetermined time; and subsequently, a determination value of the measurement oil after the degradation process is obtained by the determination method a or both of the determination method a and the determination method b. This operation is repeated until the determination value reaches a predetermined threshold value.

Although not particularly limited, the degradation process is exemplified by a Dry-TOST method described in ASTM D7873, a JCMAS-P045 method in accordance with the standards of Japan Construction Machinery and Construction Association, and a high temperature circulation degradation test method. The method for the degradation process needs to be a method capable of providing a similarity to a degradation tendency in an actual machine.

The high temperature circulation degradation test method uses a high temperature circulation degradation device (COST device). The high temperature circulation degradation device includes a container, air blowing unit, circulation pump, copper coil, and heater. The air blowing unit blows air to a sample oil in the container. The sample oil in an oil storage of the container is pumped by the circulation pump to be discharged to an upper part of the container. The sample oil discharged to the upper part of the container is circulated to the oil storage of the container through the copper coil heated by the heater. The high temperature circulation degradation test can be conducted using the high temperature circulation degradation device under the following conditions. A circulation cycle of the lubricating oil in the COST device can be converted into a working time of the device until the lubricating oil reaches the usage management reference value and the oil change reference value.

In the third step, based on the time of the degradation process in the second step, the determination value of the measurement oil after the degradation process, which is obtained in the second step, and the determination value of the measurement oil obtained in the first step, a relationship therebetween is plotted in a graph, so that a lifetime expectancy of the used lubricating oil can be predicted.

The predetermined threshold value for obtaining the determination value can be determined based on the usage limit value of the lubricating oil (i.e., a residue of an antioxidant and a color difference ($\Delta E$ or maximum color difference) of substances captured by filtration when a 50% point of an RPVOT retention ratio is defined as the usage management reference value and a 25% point of the RPVOT retention ratio is defined as the oil change reference value). When at least the two threshold values are determined, the relationship can be shown in a graph and the lifetime expectancy of the used lubricating oil can be predicted.

According to the method for predicting the lifetime expectancy of the lubricating oil in the exemplary embodiment, the usage limit time of the measurement oil adapted to predict the lifetime expectancy of the lubricating oil can be easily predicted with a high accuracy.

The lifetime expectancy prediction method of the lubricating oil in the exemplary embodiment can easily determine with a high accuracy a lifetime expectancy of a turbine oil among the lubricating oil.

Modification of Embodiment(s)

The invention is not limited to the above-described exemplary embodiment(s) but includes modifications and improvements as long as the modifications and improvements are compatible with the invention.

For instance, in the management method of the lubricating oil in the exemplary embodiment, the two methods of the determination method a and the determination method are used, but the management method is not limited thereto. For instance, another determination method capable of a simple measurement may be added to the two methods, whereby three or more determination methods are usable for make a determination.

Although a Dry-TOST method described in ASTM D7873, a JCMAS-P045 method in accordance with the standards of Japan Construction Machinery and Construction Association, and a high temperature circulation degradation test are used as the degradation process in the lifetime expectancy prediction method of the lubricating oil in the exemplary embodiment, the degradation process is not limited thereto. Any process can be appropriately employed as the degradation process as long as being capable of indicating a correlation between the process time and the lifetime expectancy of the lubricating oil.

EXAMPLE(S)

Next, the invention is described in further detail with reference to Examples, but by no means limited by Examples.

Example 1

Using a new oil of a sample oil shown below and an oil solution degraded in accordance with the Dry-TOST method described in ASTM D7873 and the JCMAS-P045 method in accordance with the standards of Japan Construction Machinery and Construction Association, determination values of the respective determination methods a and b and the RPVOT value were measured.

Sample Oil: Daphne Super Turbine Oil MG 32 manufactured by Idemitsu Kosan Co., Ltd.

Specifically, as the determination method a, using a small-sized FTIR device "DialPath" manufactured by Agilent Technologies, an infrared ray absorption spectrum of the sample oil in a range of 3500 to 3300 cm$^{-1}$ was measured. An area value of an absorption peak was obtained using a calculation software capable of a base line correction and an area calculation. Based on a standard curve of the area value of the antioxidant amount obtained in advance, a content ratio of the antioxidant and the altered substance having the same functional group as that of the used antioxidant was calculated. As a pretreatment of the determination method b, the sample oil was heated at 60 degrees C. for 24 hours and left still for 72 hours. In the determination method b, 52 g of the prepared sample oil was taken and filtrated by a method in accordance with JIS B9931. At this time, n-heptane was used as a detergent solvent. The substances obtained by filtration were used for measuring a ΔE. Using a colorimetric patch analyzer (CPA method) manufactured by Hitachi Metals. Ltd. as a colorimeter, a color difference (ΔE) between a reflected light and a transmitted light was measured. An AAWP type filter having a pore diameter 0.80 μm manufactured by Millipore Corporation was used. For the measurement of the color difference, in advance, the colorimeter was corrected using an unused clean filter. An RPVOT value (unit: min) of the sample oil was measured by a method described in ASTM D2272.

Next, the sample oil was subjected to a degradation process in accordance with the Dry-TOST method described in ASTM D7873 and the JCMAS-P045 method in accordance with the standards of Japan Construction Machinery and Construction Association. Every time a predetermined time elapsed, determination values of the respective determination methods a and b were measured or calculated and the RPVOT value was measured. With respect to the determination value in the determination method a, an effective antioxidant residual ratio (unit: %) was calculated according to a numerical formula (F1).

Effective antioxidant residual ratio (%)=(Total Content of Antioxidant and Altered Substance having Antioxidant Function after Degradation Process of Sample Oil/Content of Initial Antioxidant in Sample Oil)×100     (F1)

Figure 4:
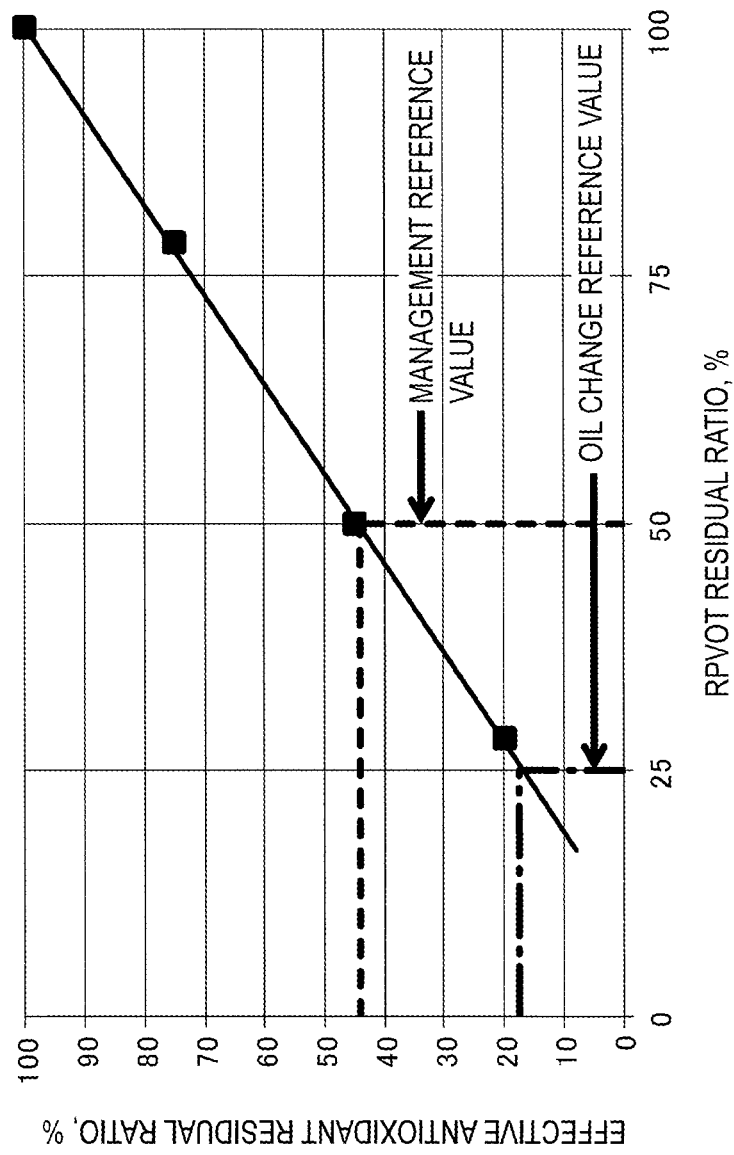
FIG. 4 is a graph showing a relationship between an effective antioxidant residual ratio and an RPVOT residual ratio in a sample oil in Example 1.
Figure 5:
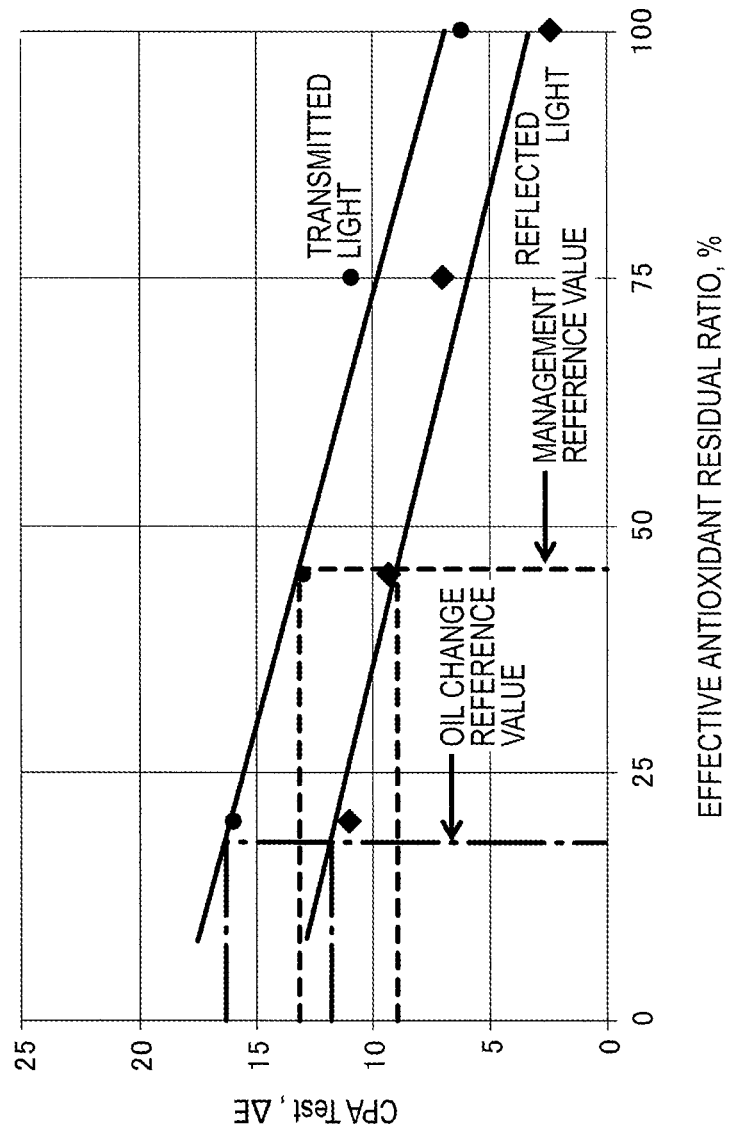
FIG. 5 is a graph showing a relationship between the effective antioxidant residual ratio and a color difference of captured substances in the sample oil in Example 1.

The obtained results are shown in FIGS. 4 and 5. As shown in FIG. 4, it was confirmed that there was a correlation between an RPVOT retention ratio (also referred to as an RPVOT residual ratio provided that a new oil accounts for 100%) and the effective antioxidant residual ratio (i.e., a value provided that a new oil accounts for 100%). Moreover, as shown in FIG. 5, it was confirmed that there was a correlation between the ΔE measured by the CPA method and the effective antioxidant residual ratio. In other words, by managing the lubricating oil based on the determination values by the determination method a and the determination method b, the degradation degree of the lubricating oil can be determined at an accuracy equivalent to that using the RPVOT value. Since the determination method a and the determination method b are easier than the measurement of the RPVOT value, it is confirmed that the degradation degree of the lubricating oil can be easily determined at a high accuracy according to the management method of the lubricating oil in Example 1.

Example 2

The sample oil in a form of a new oil and the sample oil in a form of an oil actually used in a machine (used time: about 30,600 hours) were prepared and measured in terms of the respective determination values by the determination method a and the determination method b. Sample Oil: Daphne Super Turbine Oil MG 32 manufactured by Idemitsu Kosan Co., Ltd.

Specifically, as the determination method a, using a small-sized FTIR device "DialPath" manufactured by Agilent Technologies, an infrared ray absorption spectrum of the sample oil in a range of 3500 to 3300 cm$^{-1}$ was measured. An area value of an absorption peak was obtained using a calculation software capable of a base line correction and an area calculation. Based on a standard curve of the area value of the antioxidant amount obtained in advance, a content ratio of the antioxidant and the altered substance having the same functional group as that of the used antioxidant was calculated.

The new oil and the oil actually used in a machine were subjected to the degradation process according to the high temperature circulation degradation test using the high temperature circulation degradation device (COST device). Every time a predetermined time elapsed, a determination value of the determination method a was calculated. With respect to the determination value in the determination method a, an effective antioxidant residual ratio (unit: %) was calculated according to the above numerical formula (F1). Conditions in the high temperature circulation degradation test are shown as follows.

For setting the COST conditions, RPVOT values at every used time of the oil in the machine were measured in advance and it was checked at which time the determination value by the determination method a was less than a threshold value (i.e., the usage management reference value and the oil change reference value). Next, the COST test was conducted using a new oil. RPVOT values were measured at every measurement time of the new oil until the determination value by the determination method a reached less than the threshold value (i.e., the usage management reference value and the oil change reference value) and it was examined whether the measured RPVOT values had the same degradation tendency. In the case of the same degradation tendency, the circulation cycle of the oil in the COST test is convertible into the time of the oil actually used in a machine.

Oil Amount: 250 mL
Temperature: 240 degrees C.
Oil Circulation Amount: 1 g/min
Air Amount: 20 L/hr
Sampling Time: 0 to 600 min.

Figure 6:
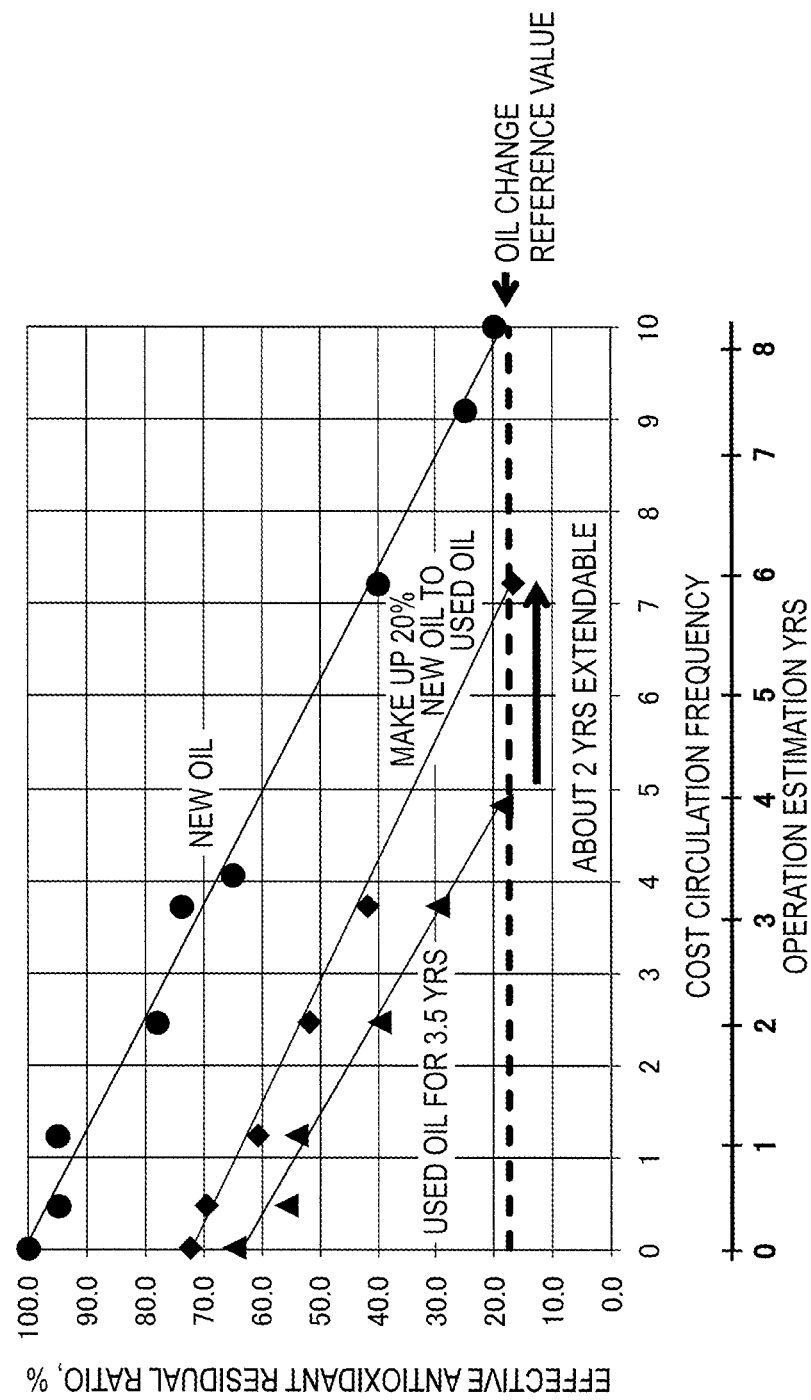
FIG. 6 is a graph showing a relationship between an effective antioxidant residual ratio and a COST circulation cycle in a measurement oil in Example 2.

Next, FIG. 6 is a graph showing a relationship between the effective antioxidant residual ratio of the new oil to the oil actually used in a machine and the COST circulation cycle. A lifetime expectancy of each of the new oil and the used oil can be obtained from the graph.

A measurement oil (an object) subjected to the lifetime expectancy prediction method of the lubricating oil was prepared. The measurement oil is a mixture of 20 mass % of the new oil and 80 mass % of the used oil (a make-up amount: 20 mass %). The measurement oil was subjected to the degradation process according to the high temperature circulation degradation test using the high temperature circulation degradation device (COST device). Every time a predetermined time elapsed, a determination value of the determination method a was calculated. It was checked at which time the determination value by the determination method a was less than the threshold value (i.e., the usage management reference value and the oil change reference value). The relationship between the effective antioxidant residual ratio of the measurement oil and the COST circulation cycle was plotted as shown in FIG. 6. A lifetime expectancy of the measurement oil can be obtained from the graph.

Moreover, as shown in FIG. 6, by comparison between the lifetime expectancy of the used oil and the lifetime expectancy of the made-up measurement oil, it can be confirmed that the lifetime expectancy can be extended by about two years by 20 mass % make-up.

Example 3

Using the new oil of the sample shown below and the oil solution degraded in accordance with the Dry-TOST method described in ASTM D7873 and the JCMAS-P045 method in accordance with the standards of Japan Construction Machinery and Construction Association as used in Example 1, a measurement was conducted according to the (ii) method of the determination method b. It should be noted that the RPVOT value and the color difference (ΔE) value measured in Example 1 were used.

Specifically, about 70 g of the sample oil was taken at the room temperature. A maximum color difference (R-B) of the sample oil was measured at a sample temperature of 25 to 30 degrees C. using a lubricating oil condition monitor sensor manufactured by Nabtesco Corporation.

Figure 7:
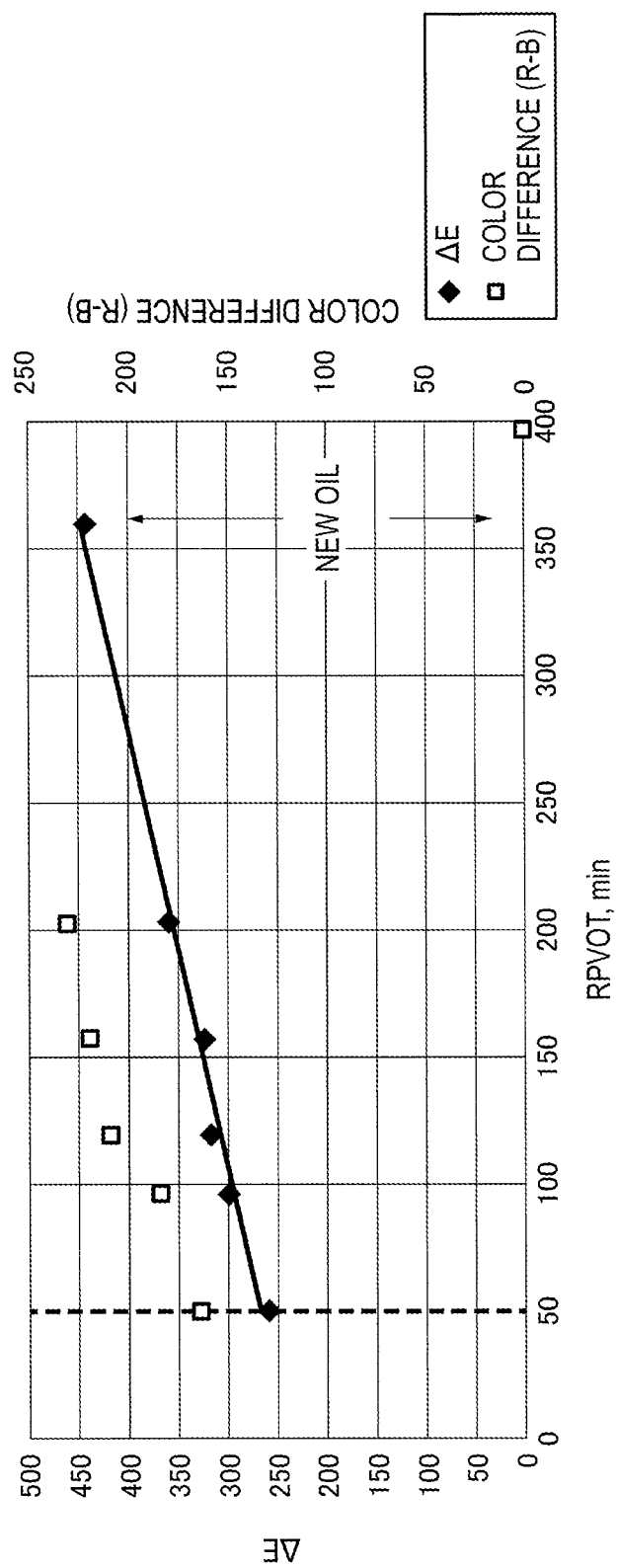
FIG. 7 is a graph showing a relationship of an RPVOT value with respect to a color difference of captured substances and a color difference of a lubricating oil in a sample oil in Example 3.

The obtained results are shown in FIG. 7. As shown in FIG. 7, it was confirmed that the RPVOT value was correlated with the color difference (ΔE) and the maximum color difference (R-B). In other words, by managing the lubricating oil based on the determination value obtained by the (ii) method of the determination method b, the degradation degree of the lubricating oil can be determined at an accuracy equivalent to the RPVOT value. Since the (ii) method of the determination method b is also easier than the measurement of the RPVOT value in the same manner as the (i) method of the determination method b, it was confirmed that the degradation degree of the lubricating oil can be easily determined at a high accuracy according to the management method of the lubricating oil in Example 3.

The invention claimed is:

1. A management method of a lubricating oil, the method comprising:
   determining a degradation degree of the lubricating oil comprising an antioxidant according to a determination method a and a determination method b,
   wherein:
   the determination method a comprises:
     measuring an infrared ray absorption spectrum of the lubricating oil with a Fourier transform infrared spectrometer, and
     calculating a total content of the antioxidant and an altered substance having the same functional group as the antioxidant to determine a deterioration degree of the lubricating oil from the total content; and
   the determination method b comprises:
     filtrating the lubricating oil with a filter,
     subsequently measuring a color difference of substances captured by the filter with a colorimeter, or measuring a color difference of the lubricating oil with the colorimeter, and
     determining a degradation degree of the lubricating oil and a mixture degree of foreign substances based on the color difference of the substances or the color difference of the lubricating oil.

2. The management method of the lubricating oil according to claim 1, wherein the Fourier transform infrared spectrometer satisfies the following:
   interference pattern: high-throughput Michelson interferometer;
   resolution: 4 $cm^{-1}$ or more; and
   cell material: ZnSe.

3. The management method of the lubricating oil according to claim 1, wherein the colorimeter is configured to measure a color difference in an RGB color space or an L*a*b* color space.

4. The management method of the lubricating oil according to claim 1, wherein the colorimeter is configured to measure a color difference in an RGB color space.

5. A lifetime expectancy prediction method of a measurement oil by determining a degradation degree of the measurement oil in a form of a used lubricating oil comprising an antioxidant, the method comprising:
   obtaining a determination value of the measurement oil according to a determination method a and a determination method b) below;
   subjecting the measurement oil to a degradation process for a predetermined time until the lubricating oil reaches a threshold value representing a usage limit of the lubricating oil, and obtaining a determination value of the measurement oil after being subjected to the degradation process according to the determination method a and the determination method below; and
   predicting a lifetime expectancy of the measurement oil based on a time of the degradation process in the subjecting step, the determination value, which is obtained in the subjecting step, of the measurement oil after being subjected to the degradation process, and the determination value, which is obtained in the obtaining step, of the measurement oil,
   wherein:
   the determination method a comprises:
     measuring an infrared ray absorption spectrum of the lubricating oil with a Fourier transform infrared spectrometer, and
     calculating a total content of the antioxidant and an altered substance having the same functional group as the antioxidant to determine a deterioration degree of the lubricating oil from the obtained content, and
   the determination method b comprises:
     filtrating the lubricating oil with a filter,
     subsequently measuring a color difference of substances captured by the filter with a colorimeter, or measuring a color difference of the lubricating oil with the colorimeter, and
     determining a degradation degree of the lubricating oil and a mixture degree of foreign substances based on the color difference of the substances or the color difference of the lubricating oil.

* * * * *